United States Patent
Qiu et al.

(10) Patent No.: US 10,405,801 B2
(45) Date of Patent: Sep. 10, 2019

(54) DISPLAY PANEL HAVING HEALTH MONITORING FUNCTION, MANUFACTURE METHOD THEREOF AND DISPLAY DEVICE

(71) Applicants: BOE TECHNOLOGY GROUP CO., LTD., Beijing (CN); ORDOS YUANSHENG OPTOELECTRONICS CO., LTD., Ordos, Inner Mongolia (CN)

(72) Inventors: Yun Qiu, Beijing (CN); Jiuxia Yang, Beijing (CN)

(73) Assignees: BOE TECHNOLOGY GROUP CO., LTD., Beijing (CN); ORDOS YUANSHENG OPTOELECTRONICS CO., LTD., Ordos, Inner Mongolia (CN)

(*) Notice: Subject to any disclaimer, the term of this patent is extended or adjusted under 35 U.S.C. 154(b) by 480 days.

(21) Appl. No.: 14/913,492

(22) PCT Filed: Sep. 29, 2015

(86) PCT No.: PCT/CN2015/091035
§ 371 (c)(1),
(2) Date: Feb. 22, 2016

(87) PCT Pub. No.: WO2016/155274
PCT Pub. Date: Oct. 6, 2016

(65) Prior Publication Data
US 2017/0035359 A1 Feb. 9, 2017

(30) Foreign Application Priority Data
Mar. 30, 2015 (CN) .......................... 2015 1 0146219

(51) Int. Cl.
A61B 5/00 (2006.01)
H01L 27/144 (2006.01)
(Continued)

(52) U.S. Cl.
CPC ........ *A61B 5/6887* (2013.01); *A61B 5/02416* (2013.01); *A61B 5/02438* (2013.01);
(Continued)

(58) Field of Classification Search
CPC . H01L 27/144; A61B 5/02416; A61B 5/6887; G06F 3/0412
See application file for complete search history.

(56) References Cited

U.S. PATENT DOCUMENTS

2002/0052192 A1* 5/2002 Yamazaki ............ G06K 9/0004
455/411
2002/0120203 A1 8/2002 Higurashi et al.
(Continued)

FOREIGN PATENT DOCUMENTS

CN 101911159 A 12/2010
CN 102413761 A 4/2012
(Continued)

OTHER PUBLICATIONS

Second Chinese Office Action dated Mar. 22, 2017; Appln. No. 201510146219.7.
(Continued)

*Primary Examiner* — Abbas I Abdulselam
(74) *Attorney, Agent, or Firm* — Ladas & Parry LLP

(57) ABSTRACT

A display panel having health monitoring function, including a first substrate; a second substrate; and a monitoring unit. The monitoring unit is configured to monitor a change in human physiological information and is disposed on the first substrate or the second substrate through a patterning process. Such display panel having health monitoring function solves the technical problem that existing display panels having health monitoring function are poor in level of integration with incompact structures.

15 Claims, 4 Drawing Sheets

(51) Int. Cl.
*A61B 5/024* (2006.01)
*G06F 3/041* (2006.01)
*H01L 27/12* (2006.01)
*G06F 3/042* (2006.01)
*A61B 5/1455* (2006.01)

(52) U.S. Cl.
CPC ........ *A61B 5/02444* (2013.01); *A61B 5/6898* (2013.01); *A61B 5/7278* (2013.01); *G06F 3/0412* (2013.01); *H01L 27/1214* (2013.01); *H01L 27/144* (2013.01); *A61B 5/14551* (2013.01); *A61B 5/742* (2013.01); *G06F 3/042* (2013.01)

(56) References Cited

U.S. PATENT DOCUMENTS

| | | | | |
|---|---|---|---|---|
| 2002/0163601 | A1* | 11/2002 | Min | G02F 1/13338 349/33 |
| 2004/0152957 | A1* | 8/2004 | Stivoric | A61B 5/01 600/300 |
| 2008/0030648 | A1* | 2/2008 | Morita | G02F 1/133611 349/64 |
| 2009/0029739 | A1* | 1/2009 | Okamoto | G02F 1/13338 455/566 |
| 2010/0256470 | A1 | 10/2010 | Miller | |
| 2010/0283765 | A1 | 11/2010 | Gotoh et al. | |
| 2012/0071734 | A1 | 3/2012 | Shimuta et al. | |
| 2012/0169962 | A1 | 7/2012 | Yuki et al. | |
| 2012/0226175 | A1 | 9/2012 | You et al. | |
| 2013/0149807 | A1* | 6/2013 | JangJian | H01L 27/1464 438/70 |
| 2014/0051200 | A1* | 2/2014 | Lin | G06F 3/0412 438/59 |
| 2015/0169136 | A1* | 6/2015 | Ganti | B06B 1/0666 345/177 |
| 2016/0045750 | A1* | 2/2016 | Drees | A61N 1/37282 607/59 |

FOREIGN PATENT DOCUMENTS

| | | |
|---|---|---|
| CN | 102576164 A | 7/2012 |
| CN | 102652669 A | 9/2012 |
| CN | 203311408 U | 11/2013 |
| CN | 203456513 U | 2/2014 |
| CN | 103961082 A | 8/2014 |
| CN | 104009067 A | 8/2014 |
| CN | 104706334 A | 6/2015 |
| JP | 2001-236476 A | 10/2001 |

OTHER PUBLICATIONS

International Search Report and Written Opinion dated Jan. 7, 2016; PCT/CN2015/091035.

First Chinese Office Action dated Aug. 3, 2016; Appln. No. 201510146219.7.

* cited by examiner

DISPLAY PANEL HAVING HEALTH MONITORING FUNCTION, MANUFACTURE METHOD THEREOF AND DISPLAY DEVICE

TECHNICAL FIELD

At least one embodiment of the present invention relates to a display panel having health monitoring function, a manufacture method thereof, and a display device.

BACKGROUND

With the popularization and application of intelligent wearable apparatus, people have paid more and more attention to health monitoring function of intelligent terminals. Currently known intelligent terminals include intelligent bracelet, watch, mobile phone and the like, in which a unit serving for monitoring a health condition is mostly separately designed.

In addition, currently known displays with relatively larger scale usually do not possess health monitoring function; even for those displays equipped with a unit for health monitoring, the unit is designed to be separated from a display panel of the display.

Therefore, most of the currently known display panels having health monitoring function are poor in level of integration, with incompact structures.

SUMMARY

Embodiments of the present invention provide a display panel having health monitoring function, a manufacture method thereof and a display device, which solve the technical problem that existing display panels having health monitoring function are poor in level of integration with incompact structures.

The display panel having health monitoring function as provided by embodiments of the present invention includes a first substrate; a second substrate; and a monitoring unit, wherein the monitoring unit is disposed on the first substrate or the second substrate through a patterning process and is configured to monitor a change in human physiological information.

In one example, the monitoring unit includes an optical sensor.

In one example, the optical sensor is a photodiode disposed at a light-transmittance region of the first substrate or the second substrate.

In one example, the photodiode is disposed at monochrome sub-pixel locations.

In one example, the photodiode is disposed on the first substrate; the first substrate includes a thin film transistor (TFT); and at each of the monochrome sub-pixel locations, the first substrate further includes electrodes disposed at both sides of the photodiode.

In one example, the electrodes disposed at both sides of the photodiode are a first transparent electrode and a second transparent electrode; wherein the first transparent electrode is electrically connected to a drain electrode of the TFT, and the first transparent electrode is disposed closer to the drain electrode as compared with the second transparent electrode.

In one example, the second transparent electrode is disposed above the first transparent electrode.

In one example, the TFT is low temperature polycrystalline silicon (LTPS) TFT or metal oxide TFT.

In one example, the photodiode includes an n-type silicon pattern layer, a p-type silicon pattern layer, and an intrinsic silicon pattern layer disposed between the n-type silicon pattern layer and the p-type silicon pattern layer.

In one example, the display panel further includes a sensing unit configured to sense a location touched by a human body contacted with the display panel.

In one example, the sensing unit is a touch-control unit or includes a photodiode.

The display device as provided by embodiments of the present invention includes any of the above-mentioned display panels.

In one example, the monitoring unit of the display panel includes a photodiode, and the display device further includes a computing unit and a controlling unit; wherein the computing unit is configured to compute a heart rate value from electrical signal output by the photodiode; and the controlling unit is configured to control a driving circuit to display the heart rate value on the display panel.

The manufacture method of a display device as provided by embodiments of the present invention includes a step of providing a monitoring unit on a first substrate or a second substrate through a patterning process.

In one example, the step of providing the monitoring unit includes: disposing a photodiode at monochrome sub-pixel locations on the first substrate or the second substrate.

In one example, the photodiode is disposed at green sub-pixel locations.

Embodiments of the present invention provide a display panel having health monitoring function, a manufacture method thereof and a display device. The display panel includes a first substrate and a second substrate, and further includes a monitoring unit configured to monitor a change in human physiological information; wherein the monitoring unit is disposed on the first substrate or the second substrate through a patterning process. By integrating the monitoring unit that monitors a change in human physiological information into the display panel, it can solve technical problem that the existing display panels having health monitoring function are poor in level of integration with incompact structures.

BRIEF DESCRIPTION OF THE DRAWINGS

In order to clearly illustrate the technical solution of the embodiments of the present invention, the drawings of the embodiments will be briefly described in the following.

Numeral References: 1—first substrate; 2—second substrate; 3—monitoring unit; 10—photodiode; 101—n-type silicon pattern layer; 102—intrinsic silicon pattern layer;

103—p-type silicon pattern layer; 20—thin film transistor (TFT); 201—gate electrode; 202—gate insulating layer; 203—active layer; 203a—amorphous silicon film; 2031—polycrystalline silicon layer; 2032—source region; 2033—drain region; 2034—polycrystalline silicon region; 204—source electrode; 205—drain electrode; 30—first transparent electrode; 40—second transparent electrode; 50—interlayer insulating layer; 60—planarization layer.

DETAILED DESCRIPTION

In order to make objects, technical solutions and advantages of the embodiments of the present invention apparent, the technical solutions of the embodiment will be described in a clearly and fully understandable way in connection with the drawings related to the embodiments of the present invention. It is obvious that the described embodiments are just a part but not all of the embodiments of the present invention. Based on the described embodiments herein, those skilled in the art can obtain other embodiment(s), without any inventive work, which should be within the scope of the present invention.

Unless otherwise defined, all the technical and scientific terms used herein have the same meanings as commonly understood by one of ordinary skill in the art to which the present invention belongs. The terms, such as "first," "second," or the like, which are used in the description and the claims of the present application, are not intended to indicate any sequence, amount or importance, but for distinguishing various components. Also, the terms, such as "a/an," "one," or the like, are not intended to limit the amount, but for indicating the existence of at least one. The terms, such as "include/including," "include/including," or the like are intended to specify that the elements or the objects stated before these terms encompass the elements or the objects and equivalents thereof listed after these terms, but not preclude other elements or objects. The terms, "on," "under," or the like are only used to indicate relative position relationship, and when the position of the object which is described is changed, the relative position relationship may be changed accordingly.

Hereafter, specific embodiments of the present invention are further described in more details, in which certain features and structures are omitted for clarity of explanation; however, the way of description is not intended to limit the embodiments of the invention to include only the features and structures as described herein, and the embodiments can include other necessary features and structures.

Figure 1:
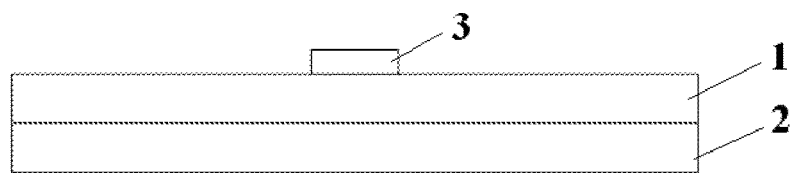
FIG. 1 is a schematic diagram illustrating a structure of a display panel as provided by an embodiment of the present invention.

Embodiments of the present invention provide a display panel having health monitoring function. As illustrated in FIG. 1, the display panel includes a first substrate 1 and a second substrate 2, and further includes a monitoring unit 3 which is configured to monitor a change in human physiological information. The monitoring unit 3 is disposed on the first substrate 1 or the second substrate 2 by a patterning process. It should be understood for those skilled in the art that, although the monitoring unit 3 in FIG. 1 is disposed centrally on a surface of the first substrate 1, it is illustrated by way of example only but not to limit the present invention thereto; in other embodiments of the present invention, the monitoring unit 3 can be disposed on the second substrate 2 or disposed at different locations on the first substrate 1, depending on actual requirements.

It should be explained that, first of all, the type of the display panel is not particularly defined in the embodiments of the present invention; for example, it can be a liquid crystal display panel so that the first substrate 1 can be an array substrate and the second substrate 2 can be a color filter substrate; of course, the display panel can also be an organic electroluminescent diode so that the first substrate 1 can be an array substrate and the second substrate 2 can be a package substrate. In practical application, the type of the display panel can be chosen according to actual demands with the only premise of integrating the above-mentioned monitoring unit 3 into the display panel.

Secondly, the human physiological information under the embodiments of the present invention can be information of blood, pulse and temperature of a human body; that is, it can be any information through which certain health indicators of a human body can be represented.

For example, the human physiological information can be blood information through which a heart rate value, as one of health indicators of a human body, can be obtained.

Embodiments of the present invention provide a display panel having health monitoring function including a first substrate 1 and a second substrate 2, and further including a monitoring unit 3 configured to monitor a change in human physiological information; wherein the monitoring unit 3 is disposed on the first substrate 1 or the second substrate 2 through a patterning process.

According to embodiments of the present invention, the monitoring unit 3 that monitors a change in human physiological information is integrated in the display panel, thus it can solve the technical problems of display panels having health monitoring function according to existing technology such as the poor integration level and the incompact structure.

In an embodiment of the present invention, the monitoring unit 3 can include an optical sensor 10 such as photodiode and infrared sensor. Generally, the optical sensor can be supplied with light from a light source separated from the display panel; for example, the light source can be a monochromatic source such as a light source capable of emitting red light or green light or blue light or infrared light, or, the light source can be other light sources capable of emitting other type of monochromatic light. Moreover, considering that corresponding sub-pixels of the above-mentioned display panel when applied in a display device are capable of emitting red light, green light and blue light, the monitoring unit in an embodiment of the present invention is an optical sensor which utilizes monochromatic sources of red, green and blue light, so that the light emitted from the sub-pixels can be directly used as the incident light. In an embodiment of the present invention, the green light emitted from the green sub-pixels is used as the incident light because the green light has much better performance of transmitting through the human skin.

In an embodiment of the present invention, the monitoring unit is configured to monitor a change in human blood, based on which a heart rate value can be obtained so as to monitor the heart rate of a human body, as one of the health indicators. The human blood contains plenty of cells of different types, which can represent different reflecting and transmitting effects with respective to the light; for example, the oxygen-bearing lurid cell and the oxygen-free lurid cell in the blood both allow the green light to be reflected, while other cells in the blood allow the green light to be transmitted therethrough; as a result, during the blood flowing correspondingly with the beating of the heart, the oxygen-bearing lurid cell and oxygen-free lurid cell in the blood that represent reflecting effect with respective to the green light will be changed, which in turn changes the green light being reflected, and hence the heart rate value can be calculated. To sum up, the above-mentioned process of monitoring a change in human blood is to detect a change of cells in the blood such as the oxygen-bearing lurid cell and the oxygen-free lurid cell by means of the light being reflected.

Based on the principle above and since the blood is flowing through every and each portion of a human body including human fingers which are more easily to be contacted with the display panel as compared with other portions, embodiments of the present invention incorporate the monitoring unit into the display panel to monitor the change in the blood in a more convenient way.

In an embodiment of the present invention, the optical sensor can be photodiode used for converting an optical signal into an electrical signal; and the photodiode is disposed at a light-transmittance region on the first substrate or the second substrate.

Figure 2:
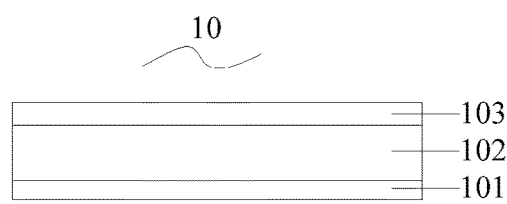
FIG. 2 is a schematic diagram illustrating a structure of a photodiode in the display panel as provided by an embodiment of the present invention.

In an example as illustrated in FIG. 2, the photodiode 10 can include a n-type silicon pattern layer 101, a p-type silicon pattern layer 103 and an intrinsic silicon pattern layer 102 disposed between the n-type silicon pattern layer 101 and the p-type silicon pattern layer 103.

Since an amount of cells in the blood flowing in the blood vessel that represent reflecting effect with respective to the light is changed with the variation of the heart rate, the reflecting condition of the light that is incident onto the human skin (for example, fingers) is also varied. The photodiode operates by following the principle of converting the optical signal into the electrical signal: the electrical energy as converted is varied depending on the type of the optical energy as absorbed; as a result, when the reflected light as absorbed changes, the electrical signal after converted is correspondingly different; in this way, it can easily calculate the heart rate value through corresponding equations according to the variation of the electrical signal.

Herein, the photodiodes are disposed at the light-transmittance region on the first substrate 1 or the second substrate 2 so that it can directly utilize the light emitted from the light-transmittance region without the need of additionally arranging a light source for supplying the photodiodes with light.

It should be noted that, first of all, the photodiode is disposed at the light-transmittance region of the first substrate 1 or the second substrate 2, that is, the photodiode is disposed at the light-transmittance regions of the sub-pixels on the first substrate 1 or the second substrate 2 so that the photodiode can directly utilize the red, green and blue light emitted from the sub-pixels and reflected by the human body.

Secondly, the photodiode 10 that is integrated on the first substrate 1 or the second substrate 2 is merely used for converting the optical signal of the reflected light into electrical signal, and the function of calculating the heart rate value from a change in the electrical signal can be performed by other units. For example, other processing units can be integrated with the photodiode 10 on a circuit board, without particularly defined herein.

As above, the technical solution of the embodiments of the present invention monitors the change in the human body by utilizing the photodiode 10. On one hand, the photodiode is simple in structure and easily to be integrated on the first substrate 1 or the second substrate 2; on the other hand, arranging the photodiode 10 in the light-transmittance region allows utilizing the light emitted from the sub-pixels of the display panel, which facilitates the integration.

In an embodiment of the present invention, considering that the display panel, when applied in a display device, emits monochromatic light in a more stable way and is less likely to result in incorrect measurement due to external disturbance, the photodiode 10 is disposed at monochrome sub-pixel locations. For example, the photodiode is disposed at all the green sub-pixel locations or all the blue sub-pixel locations or all the red sub-pixel locations on the first substrate 1 or the second substrate 2. In one example, the green light is utilized for its better performance of transmitting through the human skin; that is to say, the photodiodes 10 are disposed at all the green sub-pixel locations on the first substrate 1 or the second substrate 2. Herein, the layer in the first substrate or the second substrate where the photodiode 10 is located is not particularly defined.

In an embodiment of the present invention, the first substrate 1 is an array substrate on which the photodiode 10 is disposed; wherein the first substrate 1 includes a TFT; and at each of the monochrome sub-pixel locations, the first substrate 1 further includes electrodes disposed at both sides of the photodiode 10. For example, the monochrome sub-pixels can be green sub-pixels. For example, the electrodes disposed at both sides of the photodiode 10 can be working electrodes of the photodiode. In the present embodiment, the photodiode 10 is arranged on the array substrate because the array substrate itself requires corresponding electrode such as pixel electrode to be formed at the light-transmittance region of the sub-pixel; as a result, when the display panel is used for monitoring a change in blood, the electrode can be used as one of the working electrodes of the photodiode, so as to simplify the manufacture process of the display panel integrated with health monitoring function.

Figure 3:
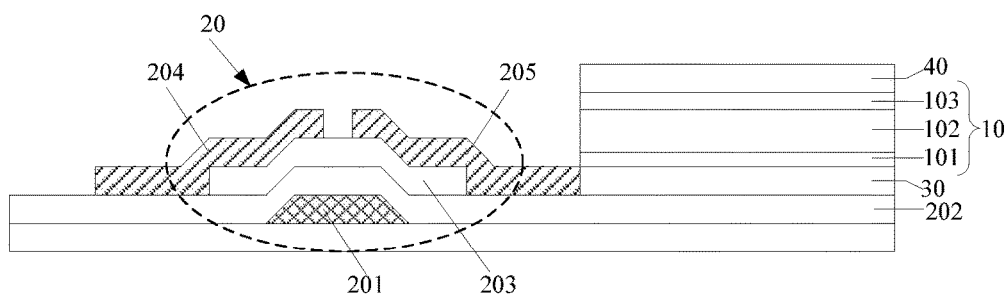
FIG. 3 is a schematic diagram illustrating a structure of a display panel integrated with a photodiode at a monochrome sub-pixel location.

In an example of the above-mentioned embodiment, the electrodes disposed at both sides of the photodiode is a first transparent electrode and a second transparent electrode; wherein the first transparent electrode is electrically connected to a drain electrode of the TFT, and wherein the first transparent electrode is disposed closer to the drain electrode as compared with the second transparent electrode. With the photodiodes being disposed at green sub-pixel locations by way of example, as illustrated in FIG. 3, at each of the green sub-pixel locations, the TFT 20 of the first substrate 1 includes a gate electrode 201, a gate insulating layer 202, an active layer 203, a source electrode 204 and a drain electrode 205; the photodiode 10 disposed between the first transparent electrode 30 and the second transparent electrode 40 can include, in sequence, a n-type silicon pattern layer 101, an intrinsic silicon pattern layer 102 and a p-type silicon pattern layer 103; wherein the first transparent electrode 30 is electrically connected to the drain electrode 205. Of course, it has no need of arranging the above-mentioned second transparent electrode 40 at sub-pixel locations of other colors because it's not necessary to arrange a photodiode 10 there. In the present embodiment, when the display panel is used for display, the second transparent electrode 40 is not applied with a voltage, so as to ensure a normal display function of corresponding sub-pixels; when the display panel is used for health monitoring, the second transparent electrode is applied with a voltage.

It should be noted that, for embodiments as illustrated in FIG. 3, the second transparent electrode 40 can also be disposed above or below the first transparent electrode 30. For example, the second transparent electrode 40 can be disposed above the first transparent electrode 30; in such case, since the TFT is formed prior to the formation of the photodiode and the second transparent electrode 40, a failure of TFT due to an excessively larger "step difference" during the manufacture process thereof can be avoided, as compared with the process in which the second transparent electrode 40 and the photodiode 10 are formed prior to the formation of the TFT.

Besides, the type of the TFT 20 is not particularly defined in the embodiments of the present invention. It can be amorphous silicon film TFT, low temperature polycrystalline silicon (LTPS) TFT, metal oxide TFT and the like. In one example, the low temperature polycrystalline silicon (LTPS) TFT or the metal oxide TFT is adopted as the TFT 20 for consideration of the relatively higher mobility rate thereof.

In an embodiment of the present invention in which the low temperature polycrystalline silicon (LTPS) TFT is used as the TFT 20 by way of example, at a monochrome sub-pixel location, a monochrome sub-pixel is manufactured by steps as below.

Figure 4:
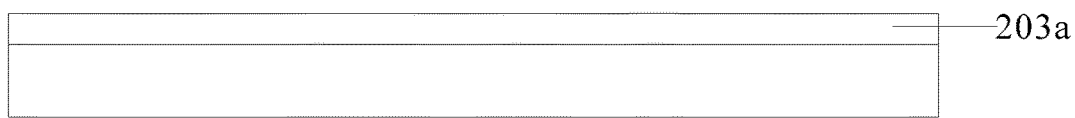
FIGS. 4-9 are schematic diagrams illustrating a process of manufacturing a sub-pixel including a photodiode, at a monochrome sub-pixel location, in a display panel as provided by an embodiment of the present invention.

S101, forming an amorphous silicon film 203$a$ on a substrate, as illustrated in FIG. 4.

For example, the amorphous silicon film 203$a$ can be formed by plasma chemical vapor deposition (PECVD) method or by sputtering method.

S102, based on a completion of step S101, placing the substrate formed with the amorphous silicon film 203$a$ into an annealing furnace for dehydrogenation treatment.

For example, the substrate can be maintained at a certain temperature in the annealing furnace for a certain period of time to reduce the hydrogen content in the amorphous silicon film; it usually has to control the hydrogen content in the amorphous silicon film to be below 3% so as to avoid an occurrence of hydrogen explosion during a subsequent laser annealing process.

For example, the dehydrogenation treatment can be performed under 400-600° C. for 20-120 minutes.

S103, based on a completion of step S102, performing an annealing treatment to the amorphous silicon film 203$a$ by using excimer laser annealing method, for example, to crystallize the amorphous silicon film 203$a$ as a polycrystalline silicon film.

Figure 5:
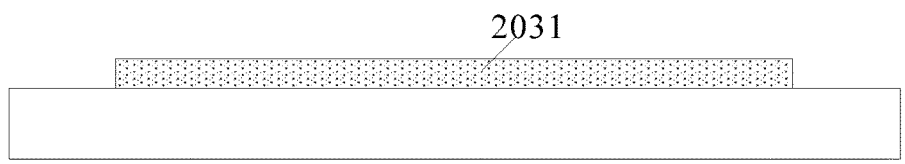

S104, based on a completion of step S103, performing a patterning process to the polycrystalline silicon film to form a polycrystalline silicon layer 2031 as illustrated in FIG. 5.

Figure 6:
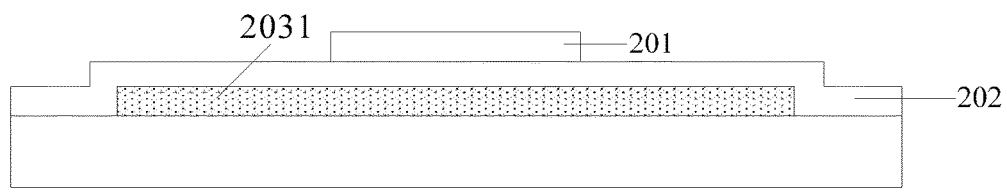

S105, based on a completion of step S104, forming a gate insulating layer 202 and a gate electrode 201, as illustrated in FIG. 6.

For example, the gate insulating layer 202 can be deposited by using PECVD method. Then, a gate metal layer can be formed on the gate insulating layer 202 by using sputtering method, and the gate electrode 201 can be formed by using a patterning process.

Figure 7:
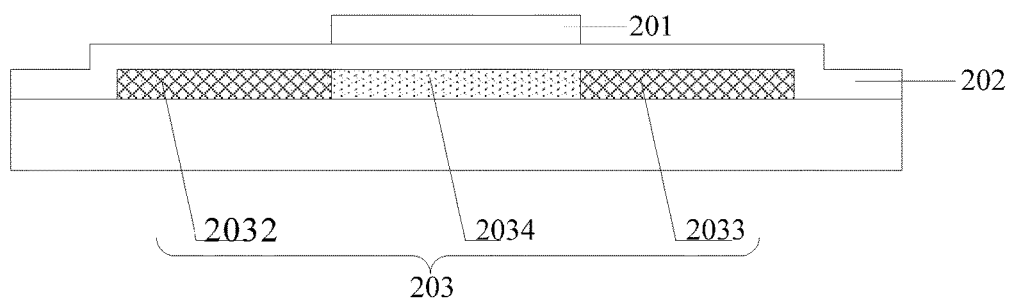

S106, based on a completion of step S105, performing an ion implantation process to a region of the polycrystalline silicon layer 2031 corresponding to a source region and a drain region, so as to form an active layer 203 as illustrated in FIG. 7. The active layer 203 includes a source region 2032, a drain region 2033 and a polycrystalline silicon region 2034 located between the source region 2031 and the drain region 2033.

For example, it can perform an activating process after the ion implantation process by using rapid thermal annealing method, laser annealing method or furnace annealing method. The furnace annealing method has relatively higher economic efficiency, is easier for implementation and obtains better homogeneity. In an embodiment of the present invention, an activating thermal process can be performed under 300-600° C. for 0.5-4 hours (1-3 hours is preferable) within the annealing furnace.

Figure 8:
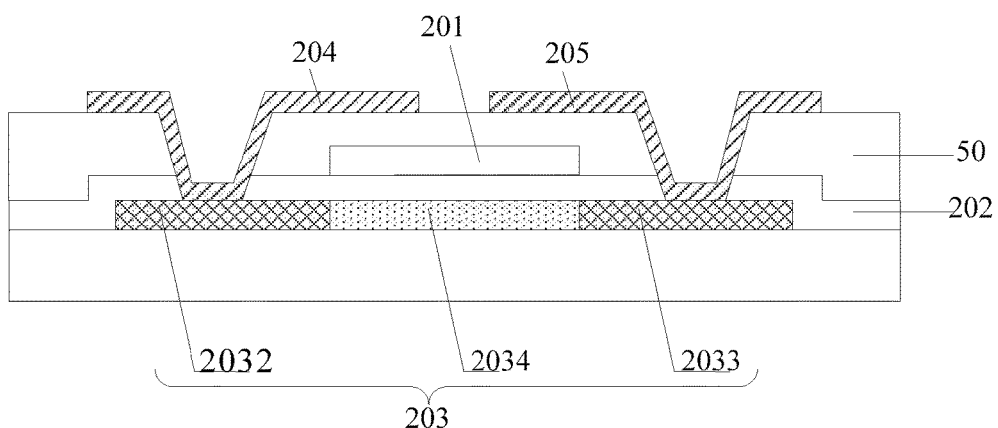
Figure 9:
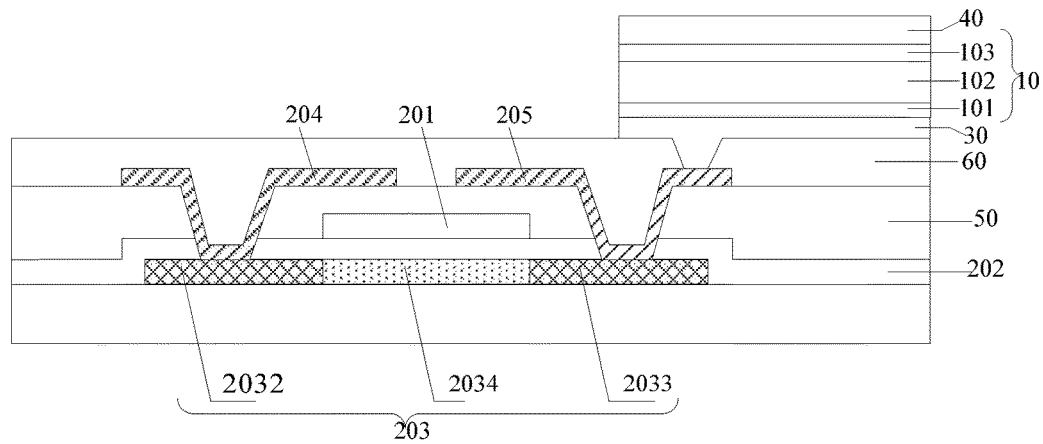

S107, based on a completion of step S106, forming an interlayer insulating layer 50, and forming a source electrode 204 and a drain electrode 205 on the interlayer insulating layer 50, as illustrated in FIG. 8. The source electrode 204 and the drain electrode 205 are contacted with the source region 2032 and the drain region 2033, respectively, by means of through holes formed in the interlayer insulating layer 50 and the gate insulating layer 202, respectively.

For example, the interlayer insulating layer 50 can be deposited by using PECVD method; then a source-drain metallic layer can be formed on the interlayer insulating layer 50 by using sputtering method; and the source electrode 204 and the drain electrode 205 can be formed by using a patterning process.

S108, based on a completion of step S107, forming a planarization layer 60, and forming a first transparent electrode 30 electrically connected to the drain electrode 205 on the planarization layer 60; and then at a green-pixel location, forming a n-type silicon pattern layer 101, an intrinsic silicon pattern layer 102, a p-type silicon pattern layer 103 and a second transparent electrode 40, in sequence, on the first transparent electrode 30.

It should be noted that FIGS. 4-9 of the present invention are merely illustrated in a simplified manner in which only structures associated with the inventive concept of the present invention are presented but those structures uncorrelated (i.e., well-known structures) are omitted or only partly presented, for purpose of clearly describing the technical solutions of embodiments of the present invention.

In addition, since switching on all the monochrome sub-pixels in the entire display screen may lead to considerable consumption of electrical energy, in an embodiment of the present invention at least one monochrome sub-pixel in an area touched by the human body, for example, fingers, is switched on; correspondingly, in such embodiments, the display panel can further include a sensing unit configured to sense a location where the human body touched with the display panel.

In embodiments of the present invention, the sensing unit can be a touch-control unit; for example, it can monitor a location of the finger by means of a touch-control electrode disposed on the display panel, and it can also monitor the location of the finger by means of photodiodes. In case where the photodiode is utilized for monitoring the location of the finger, the photodiode can be disposed at each and every sub-pixel location; upon determining the location of the finger through the photodiodes, the health monitoring function can be activated, depending on actual conditions.

Embodiments of the present invention further provide a display device including the display panel as discussed in any of the above embodiments.

The display device can be, for example, tablet PC, television, large-scaled mobile phone and the like, without limiting the present invention thereto.

Figure 10:
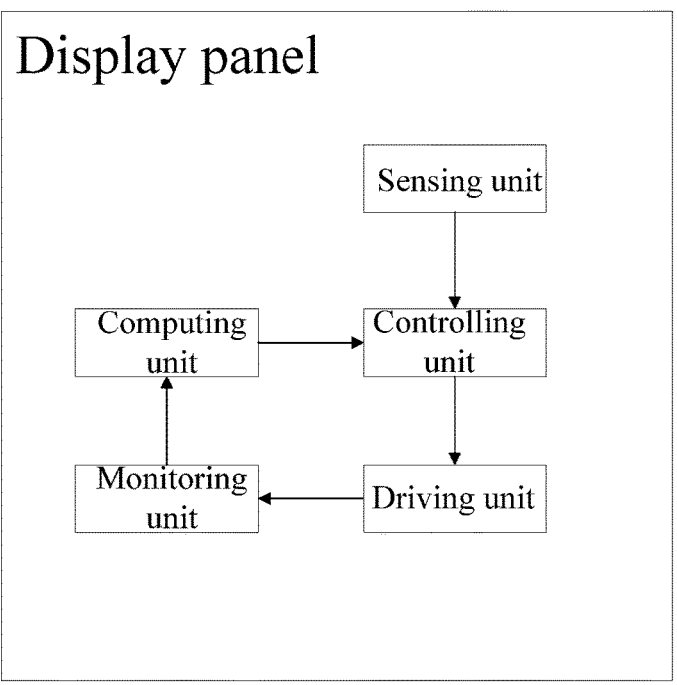
FIG. 10 is a schematic diagram illustrating a structure of a display device as provided by an embodiment of the present invention.

For example, in case that the monitoring unit is implemented by photodiode, as illustrated in FIG. 10, the display device can further include a computing unit and a controlling unit; wherein the computing unit is configured to calculate a heart rate value from electrical signal output by the photodiode (activated by, for example, the foregoing sensing unit); the controlling unit is configured to control a driving circuit to display the heart rate value on the display panel. The computing unit can be implemented by a chip disposed on a circuit board of the display panel which can realize calculating function, and the controlling unit can be implemented by a controlling chip disposed on the circuit board.

For example, in case where the display panel further includes a sensing unit, the controlling unit can be further configured to switch on a TFT of at least one monochrome sub-pixel at the location touched by the human body through the driving circuit, according to the location where the human body touched with the display panel which is determined by the sensing unit.

For example, when the controlling unit switches on the TFTs of a plurality of monochrome sub-pixels at the location touched by the human body through the driving circuit, the computing unit can calculate heart rate values from the electrical signal output by the photodiode disposed at each of the monochrome sub-pixel locations and obtain an average value thereof.

Herein it should be noted that FIG. 10 merely illustrates part of the structure of the display device as provided by embodiments of the present invention, and the remaining parts that are omitted from FIG. 10 are well-known to those skilled in the art for which no details will be described.

Figure 11:
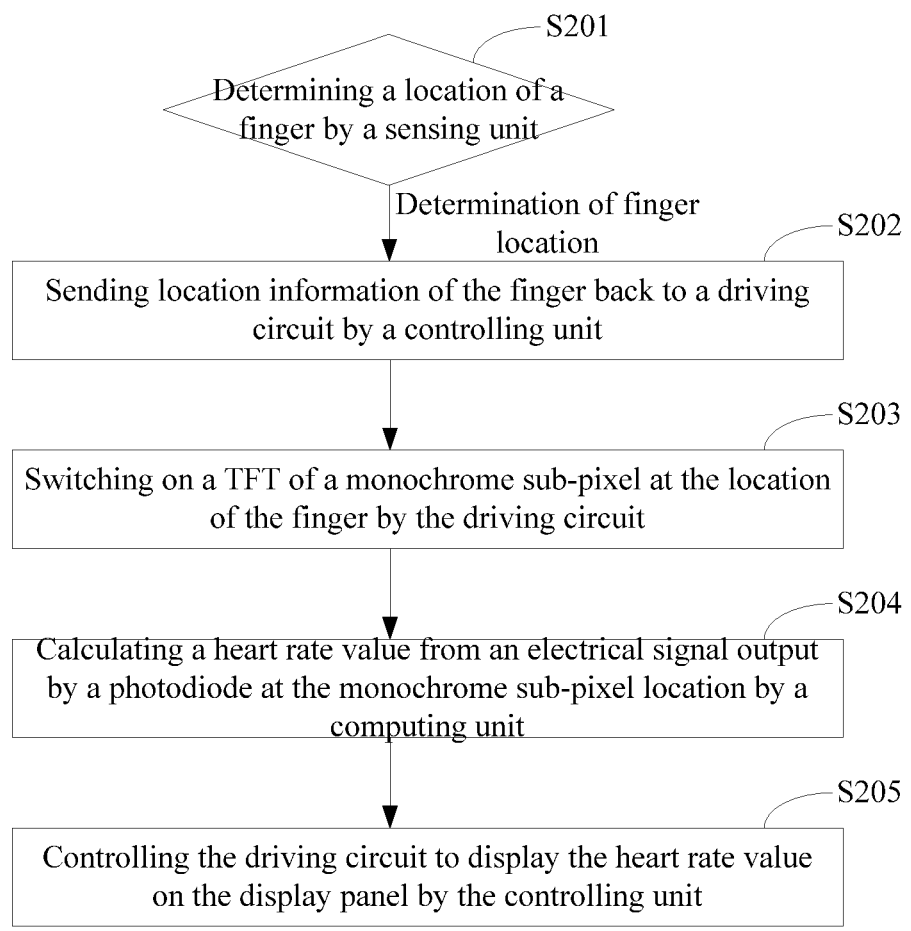
FIG. 11 is a flow chart illustrating a process of health monitoring performed by a display device as provided by an embodiment of the present invention.

In such case, as illustrated in FIG. 11, an exemplary flow chart for the display device to perform a health monitoring includes steps as below.

S201, determining a location of a finger by a sensing unit, and performing steps S202-S205 upon the location being determined.

S202, sending location information of the finger back to a driving circuit by a control ling unit.

S203, switching on a TFT of a monochrome sub-pixel at the location of the finger by the driving circuit.

S204, calculating a heart rate value from an electrical signal output by a photodiode at the monochrome sub-pixel location by a computing unit.

S205, controlling the driving circuit to display the heart rate value on the display panel by the controlling unit.

The foregoing is merely exemplary embodiments of the invention, but is not used to limit the protection scope of the invention. Those skilled in the art will readily appreciate that many modifications are possible in the foregoing embodiments, or equivalent substitutions are made for part of technical features, without departing from the spirit and the scope of the present invention. The protection scope of the invention shall be defined by the attached claims.

The present application claims priority of Chinese Patent Application No. 201510146219.7 filed on Mar. 30, 2015 titled "DISPLAY PANEL HAVING HEALTH MONITORING FUNCTION AND DISPLAY DEVICE", the disclosure of which is incorporated herein by reference in its entirety as part of the present application.

What is claimed is:

1. A display panel having health monitoring function, comprising:
   a first substrate;
   a second substrate; and
   a monitoring unit, disposed on the first substrate and configured to monitor a change in human physiological information
   wherein the monitoring unit includes a photodiode, the photodiode is disposed at a monochrome sub-pixel location, the photodiode is disposed on the first substrate, the first substrate includes a thin film transistor (TFT); and at the monochrome sub-pixel location, the first substrate further includes two electrodes disposed at both sides of the photodiode respectively, the electrodes disposed at both sides of the photodiode are a first transparent electrode and a second transparent electrode, wherein the first transparent electrode and the second transparent electrode are working electrodes of the photodiode, and the first transparent electrode is electrically connected to a drain electrode of the TFT and is a pixel electrode of the display panel.

2. The display panel of claim 1, wherein the photodiode is disposed at a green sub-pixel location.

3. The display panel of claim 2, wherein the photodiode includes a n-type silicon pattern layer, a p-type silicon pattern layer, and an intrinsic silicon pattern layer disposed between the n-type silicon pattern layer and the p-type silicon pattern layer.

4. The display panel of claim 1, wherein first transparent electrode is disposed closer to the drain electrode as compared with the second transparent electrode.

5. The display panel of claim 4, wherein the second transparent electrode is disposed above the first transparent electrode.

6. The display panel of claim 1, wherein the photodiode includes a n-type silicon pattern layer, a p-type silicon pattern layer, and an intrinsic silicon pattern layer disposed between the n-type silicon pattern layer and the p-type silicon pattern layer.

7. The display panel of claim 1, wherein the TFT is a low temperature polycrystalline silicon (LTPS) TFT or a metal oxide TFT.

8. The display panel of claim 1, further including a sensing unit, the sensing unit is configured to sense a location touched by a human body contacted with the display panel.

9. The display panel of claim 8, wherein the sensing unit is a touch-control unit or a photodiode.

10. A display device, including the display panel of any one of claim 1.

11. The display device of claim 10, wherein the display device further includes a computing unit and a controlling unit;
   wherein the computing unit is configured to compute a heart rate value from electrical signal output by the photodiode;
   the controlling unit is configured to control a driving circuit to display the heart rate value on the display panel.

12. A manufacture method of the display panel having health monitoring function according to claim 1, comprising a step of providing a monitoring unit on the first substrate or the second substrate through a patterning process.

13. The manufacture method of claim 12, wherein the step of providing the monitoring unit includes: disposing a photodiode at a monochrome sub-pixel location on the first substrate or the second substrate.

14. The manufacture method of claim 13, wherein the photodiode is disposed at a green sub-pixel location.

15. The display panel of claim 1, wherein the photodiode includes a n-type silicon pattern layer, a p-type silicon pattern layer, and an intrinsic silicon pattern layer disposed between the n-type silicon pattern layer and the p-type silicon pattern layer.

* * * * *